US012811041B2

(12) United States Patent
Chen et al.

(10) Patent No.: US 12,811,041 B2
(45) Date of Patent: Nov. 24, 2026

(54) MANUFACTURING METHOD OF MAGNETIC PARTICLES

(71) Applicant: INNOCELL TECHNOLOGY CO., LTD., Taipei City (TW)

(72) Inventors: Chien-An Chen, New Taipei City (TW); Cheng-Tai Chen, Taoyuan City (TW); Pei-Shin Jiang, Hsinchu City (TW)

(73) Assignee: INNOCELL TECHNOLOGY CO., LTD., Taipei City (TW)

( * ) Notice: Subject to any disclaimer, the term of this patent is extended or adjusted under 35 U.S.C. 154(b) by 0 days.

(21) Appl. No.: 18/185,346

(22) Filed: Mar. 16, 2023

(65) Prior Publication Data

US 2023/0245808 A1 Aug. 3, 2023

Related U.S. Application Data

(62) Division of application No. 16/226,651, filed on Dec. 20, 2018, now abandoned.

(60) Provisional application No. 62/609,343, filed on Dec. 22, 2017.

(51) Int. Cl.

| | |
|---|---|
| ***H01F 1/26*** | (2006.01) |
| ***H01F 1/00*** | (2006.01) |
| ***H01F 1/37*** | (2006.01) |
| *G01N 33/543* | (2006.01) |

(52) U.S. Cl.

CPC ............. *H01F 1/26* (2013.01); *H01F 1/0054* (2013.01); *H01F 1/37* (2013.01); *G01N 33/5434* (2013.01); *G01N 2446/10* (2013.01)

(58) Field of Classification Search

CPC ........... G01N 2446/10; G01N 33/5434; G01N 33/54346; G01N 2446/20; B22F 1/18; C08J 3/128

See application file for complete search history.

(56) References Cited

U.S. PATENT DOCUMENTS

| | | | | |
|---|---|---|---|---|
| 6,103,379 A * | 8/2000 | Margel | B01J 13/14 | 428/407 |
| 6,133,047 A * | 10/2000 | Elaissari | G01N 33/5434 | 427/127 |
| 6,525,156 B1 * | 2/2003 | Ernst | B01J 20/26 | 526/264 |

(Continued)

FOREIGN PATENT DOCUMENTS

| | | |
|---|---|---|
| JP | 2005255967 | * 9/2005 |
| JP | 3738847 | * 1/2006 |

*Primary Examiner* — Tabassom Tadayyon Eslami

(74) *Attorney, Agent, or Firm* — MUNCY, GEISSLER, OLDS & LOWE, P.C.

(57) ABSTRACT

Described herein is a manufacturing method of a magnetic particle. First, deionized water, an organic solvent, a hydrophilic polymer, a lipid-soluble initiator, and at least two monomers are placed in a reactor and then stirred for polymerizing the at least two monomers into a copolymer to form a knobby copolymer core. Next, a polymer layer is formed to cover the knobby copolymer core, wherein the polymer layer has at least one functional group. Thereafter, a magnetic substance precursor is adsorbed by the knobby copolymer core covered with the polymer layer to form a magnetic substance layer. Further, a silicon-based layer may be additionally formed to cover the magnetic substance layer.

8 Claims, 4 Drawing Sheets

(56) References Cited

U.S. PATENT DOCUMENTS

2009/0017518 A1* 1/2009 Wu ........................ B82Y 25/00
428/404

* cited by examiner

MANUFACTURING METHOD OF MAGNETIC PARTICLES

CROSS REFERENCE TO RELATED APPLICATION

This application is a divisional application of and claims the priority benefit of U.S. application Ser. No. 16/226,651, filed on Dec. 20, 2018, now pending, which claims the priority benefit of U.S. provisional application Ser. No. 62/609,343, filed on Dec. 22, 2017. The entirety of each of the above-mentioned patent applications is hereby incorporated by reference herein and made a part of specification.

TECHNICAL FIELD

The disclosure is related to a manufacturing method of magnetic particle.

BACKGROUND

Micron-sized magnetic particles have been widely used in the field of biomedicine, such as in immune-quantitative analysis, purification and separation, or cell stimulation and amplification. However, currently commercial magnetic particles are all spheres, and spheres provide only a minimum surface area in an equal volume object, which may not conform to the biomimetic concept in practical applications, and thus is not the most ideal type in many applications. Therefore, there is an urgent need to develop magnetic particles that provide larger surface area and conform to the biomimetic concept simultaneously.

SUMMARY

The disclosure provides a manufacturing method of a magnetic particle, in which the magnetic particle includes a knobby surface.

The manufacturing method of the magnetic particle of the present disclosure includes the following steps. First, placing deionized water, an organic solvent, a hydrophilic polymer, a lipid-soluble initiator, and at least two monomers in a reactor, and then stirring for polymerizing the at least two monomers into a copolymer to form a knobby copolymer core. Next, forming a polymer layer to cover the knobby copolymer core is performed, in which the polymer layer has at least one functional group. Thereafter, adsorbing a magnetic substance precursor is performed by the knobby copolymer core covered with the polymer layer to form a magnetic substance layer. Further, a silicon-based layer may be additionally formed to cover the magnetic substance layer.

In an embodiment of the present disclosure, the aforementioned at least two monomers include monofunctional monomer and bifunctional monomer.

In an embodiment of the present disclosure, the volume percentage of the aforementioned bifunctional monomer relative to the monofunctional monomer is 0.4% to 2%.

In an embodiment of the present disclosure, the volume percentage of the aforementioned bifunctional monomer relative to the monofunctional monomer is 0.5% to 1.8%.

In an embodiment of the present disclosure, the volume percentage of the aforementioned bifunctional monomer relative to the monofunctional monomer is 0.6% to 1.5%.

In an embodiment of the present disclosure, the aforementioned knobby copolymer core includes a styrene/divinylbenzene copolymer, a methyl methacrylate/triethylene glycol dimethacrylate copolymer, a methyl methacrylate/ethylene glycol dimethacrylate copolymer, a styrene/triethylene glycol dimethacrylate copolymer, a styrene/ethylene glycol dimethacrylate copolymer, or a methyl methacrylate/divinylbenzene copolymer.

In an embodiment of the present disclosure, the aforementioned at least one functional group includes a carboxyl group, an amine group, or a combination thereof.

In an embodiment of the present disclosure, the aforementioned magnetic substance layer comprises an iron ion ($Fe^{2+}$), a cobalt ion ($Co^{2+}$), a nickel ion ($Ni^{2+}$), or a combination thereof.

In an embodiment of the present disclosure, the aforementioned magnetic substance precursor comprises ferrous chloride, cobalt chloride, or nickel chloride.

In an embodiment of the present disclosure, the aforementioned silicon-based layer comprises siloxane, silica glass, silicon oxide, silicate salt or a combination thereof.

In an embodiment of the present disclosure, the aforementioned at least two monomers comprise a lipid-soluble monovinyl monomer, and a lipid-soluble divinyl monomer.

In an embodiment of the present disclosure, the aforementioned lipid-soluble monovinyl monomer comprises styrene or methyl methacrylate.

In an embodiment of the present disclosure, the aforementioned lipid-soluble divinyl monomer comprises divinylbenzene, ethylene glycol dimethacrylate, or triethylene glycol dimethacrylate.

The magnetic particle being manufactured by the manufacturing method of the magnetic particle of the present disclosure may include the following properties.

In an embodiment of the present disclosure, the aforementioned knobby copolymer core comprises a plurality of protrusions, and an average height of the plurality of protrusions is 100 nm to 5000 nm.

In an embodiment of the present disclosure, an average diameter of the magnetic particle is 1 μm to 8.5 μm.

In an embodiment of the present disclosure, a thickness of the aforementioned magnetic substance layer is 20 nm to 200 nm.

In an embodiment of the present disclosure, a thickness of the aforementioned silicon-based layer is at least 1 nm to 50 nm.

Based on the above, the magnetic particle of an embodiment of the disclosure has multi-protrusive surface, so that the surface area of the magnetic particles can be greatly increased, thereby contributing to the close packing of the magnetic particles. Furthermore, since the surface of the knobby polymer particles is formed with a polymer layer containing at least one functional group and the functional group may be charged, it is advantageous for the knobby polymer particles to adsorb more magnetic substance precursors. Accordingly, the effect of high magnetic quantization is achieved.

Several exemplary embodiments accompanied with figures are described in detail below to further describe the disclosure in details.

DETAILED DESCRIPTION OF DISCLOSED EMBODIMENTS

Figure 1:
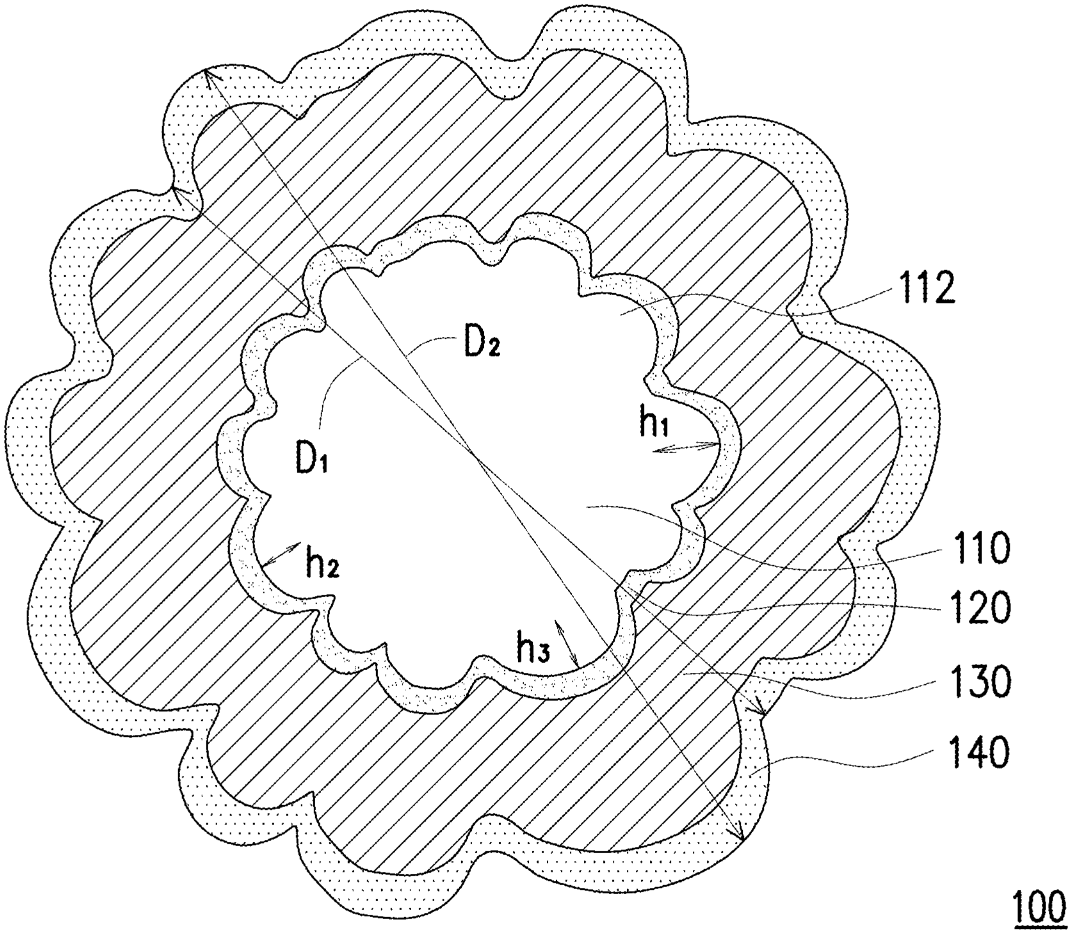
FIG. 1 is a schematic diagram of a magnetic particle in accordance with an embodiment of the present disclosure.

FIG. 1 is a schematic diagram of a magnetic particle in accordance with an embodiment of the present disclosure. The magnetic particle 100 includes in the order of a knobby copolymer core 110, a polymer layer 120, a magnetic substance layer 130, and a silicon-based layer 140 from the inside to the outside. In which, the knobby copolymer core 110 is spherical and has a plurality of protrusions 112 on its surface.

The aforementioned magnetic particle 100 has an average diameter D, that is, an average value of the shortest diameter (for example, D1) and the longest diameter (for example, D2) of the magnetic particles 100, and may range from 1 μm to 50 μm. In an embodiment, the magnetic particle 100 may have an average diameter of 2 μm to 40 μm. In another embodiment, the magnetic particle 100 may have an average diameter of 3 μm to 30 μm. In still another embodiment, the magnetic particle 100 may have an average diameter of 4 μm to 20 μm.

Moreover, the average height h of the aforementioned protrusions 112, that is, the average value of the vertical distance from the top side of each protrusion 112 to the connection line between the two bottom sides of each protrusion 112 (for example, height h1, h2, h3). The average height h of the protrusions 112 may range from 100 nm to 5000 nm, for example, 100 nm to 500 nm, 500 nm to 1000 nm, 1000 nm to 1500 nm, 1500 nm to 2000 nm, 2000 nm to 2500 nm, 2500 nm to 3000 nm, 3000 nm to 3500 nm, 3500 nm to 4000 nm, 4000 nm to 4500 nm or 4500 nm to 5000 nm. In an embodiment, the protrusions 112 may have an average height h of 300 nm to 4000 nm. In another embodiment, the protrusions 112 may have an average height h of 500 nm to 3000 nm. In yet another embodiment, the protrusions 112 may have an average height h of 800 nm to 2000 nm. In still another embodiment, the protrusions 112 may have an average height h of 1000 nm to 1800 nm.

In an embodiment of the aforementioned magnetic particles, the protrusions 112 may be uniformly or non-uniformly distributed on the surface, and as a whole, the protrusions 112 are substantially irregular protrusions. For example, the protrusion 112 may include, but are not limited to, a papillary shape or a spherical shape. In addition, in an embodiment, the method for forming the knobby copolymer core 110 may include, but is not limited to, a dispersion polymerization method, a suspension polymerization method, or an emulsion polymerization method, that is, at least two monomers are polymerized into a copolymer via the above polymerization methods. In an embodiment, the at least two monomers may be lipid-soluble monomers, and may include monofunctional monomer or bifunctional monomer, in which the volume percentage of the bifunctional monomer relative to the monofunctional monomer may be 0.4% to 2%, such as 0.5% to 1.8% or 0.6% to 1.5%.

The aforementioned monofunctional monomer may be a monovinyl monomer, such as styrene, methyl methacrylate, or other monofunctional monomers. The bifunctional monomer may be a divinyl monomer, such as divinylbenzene, ethylene glycol dimethacrylate, triethylene glycol dimethacrylate, or other bifunctional monomers. In an embodiment, the copolymer may include a styrene/divinylbenzene copolymer, a methyl methacrylate/triethylene glycol dimethacrylate copolymer, a methyl methacrylate/ethylene glycol dimethacrylate copolymer, a styrene/triethylene glycol dimethacrylate copolymer, a styrene/ethylene glycol dimethacrylate copolymer, or a methyl methacrylate/divinylbenzene copolymer, but is not limit thereto.

The aforementioned polymer layer 120 may cover the knobby copolymer core 110, and the polymer layer 120 may include at least one functional group. In an embodiment, the material of the polymer layer 120 is different from the knobby copolymer core 110. Further, the functional group may be charged, so that the surface of the knobby copolymer core 110 may be charged, which facilitates the subsequent adsorption of the magnetic substance precursor to form the magnetic substance layer 130. In addition, in an embodiment, the functional group may be negatively charged, and the functional group may be a carboxyl group, an amine group, or a combination thereof, but is not limited thereto.

It should be mentioned that, although the polymer layer 120 and the knobby copolymer core 110 are depicted as distinguishable layers in FIG. 1, the polymer layer 120 and the knobby copolymer core 110 actually do not exist clear boundaries. Further, in the present disclosure, a film layer having a functional group and located on the surface of the knobby copolymer core is collectively referred to as a polymer layer, in practice, however, the polymer layer 120 may be the surface of the knobby copolymer core modified by a functional group, rather than specifically forming a film layer.

The aforementioned magnetic substance layer 130 may cover the polymer layer 120. In an embodiment, the knobby copolymer core 110 covered with the polymer layer 120 may adsorb the magnetic substance precursor to form the magnetic substance layer 130 on the polymer layer 120. In an embodiment, the magnetic substance precursor may include, but is not limited to, an iron ion ($Fe^{2+}$), a cobalt ion ($Co^{2+}$), a nickel ion ($Ni^{2+}$), or a combination thereof. Specifically, the magnetic substance precursor may be a salt of the aforementioned metal ions, such as ferrous chloride, cobalt chloride, nickel chloride, or the like. In an embodiment, the surface of the magnetic substance layer 130 may have small protrusions, that is, have a rough surface. Further, the magnetic substance layer 130 may include, but is not limited to, a paramagnetic substance, a superparamagnetic substance, a ferromagnetic substance, a ferrite magnetic substance, or a combination thereof. In an embodiment, the magnetic substance layer 130 may be a ferromagnetic substance. Also, in an embodiment, the magnetic substance layer 130 may have a substantially uniform thickness and entirely cover the knobby copolymer core 110. For example, the thickness of the magnetic substance layer 130 may be 20 nm to 200 nm, and may be, for example, 30 nm to 180 nm, 40 nm to 150 nm or 50 nm to 120 nm.

The aforementioned silicon-based layer 140 may cover the magnetic substance layer 130. In an embodiment, the material of the silicon-based layer 140 may include, but is not limited to, siloxane, silicon glass, silicon oxide, silicate, or a combination thereof. Specifically, the silicon-based layer 140 may include a material such as tetramethoxysilane (TMOS), tetraethoxysilane (TEOS), 3-aminopropyltriethoxysilane (APTES), 3-glycidoxypropyltrimethoxysilane (GOPTS), or the like, but is not limited thereto. Moreover, in an embodiment, the thickness of the silicon-based layer 140 may be 1 nm to 50 nm, and may be 5 nm to 40 nm, 10 nm to 35 nm, or 15 nm to 30 nm.

In particular, since the polymer layer 120, the magnetic substance layer 130, and the silicon-based layer 140 sequentially formed on the knobby copolymer core 110 do not substantially change the morphology of the knobby copolymer core 110, the resulting magnetic particles 100 still have knobby appearance. As a result, the surface area of the magnetic particles 100 can be greatly increased, and the close packing of the magnetic particles 100 is facilitated.

Furthermore, since the material constituting the magnetic particles 100 is substantially biocompatible, the magnetic particles 100 can be widely applied to the field of biomedicine.

In an embodiment, the manufacturing method of the magnetic particles may include the following steps. First, a knobby copolymer core is produced. Specifically, deionized water, an organic solvent, a hydrophilic polymer, a lipid-soluble initiator, a lipid-soluble monovinyl monomer and a lipid-soluble divinyl monomer are performed to place into a reactor. Next, the aforementioned mixture was stirred for at least 20 hours at 60 to 90° C. under a nitrogen atmosphere.

In an embodiment, the aforementioned deionized water may be added in an amount of 0 to 10 ml. Also, the aforementioned organic solvent may be added in an amount of 10 to 70 ml, and is, for example, an alcohol, an ether, or the like. For example, the organic solvent used may include, but is not limited to, ethanol, propanol, isopropanol, tert-butanol, n-hexanol or ethylene glycol methyl ether. Further, the aforementioned hydrophilic polymer may be added in an amount of 0.1 to 1 g, and is, for example, polyvinylpyrrolidone, polyvinyl alcohol, polyethylene glycol, a copolymer of vinyl acetate and vinylamine, cellulose and derivatives thereof, a saccharide, a collagen, a polyamino acid, or the like, but is not limited thereto. In addition, the aforementioned lipid-soluble initiator may be added in an amount of 0.3 to 1.5 g, and is, for example, Azobisisobutyronitrile (AIBN), Benzoyl peroxide (BPO), Lauroyl peroxide (LPO), or the like, but is not limited thereto. Moreover, the aforementioned lipid-soluble monovinyl monomer may be added in an amount of 5 to 15 ml, and is, for example, styrene, methyl methacrylate (MMA), or the like, but is not limited thereto. Furthermore, the content of the aforementioned lipid-soluble divinyl monomer may be 0.4% to 2% by volume of the content of the lipid-soluble monovinyl monomer, and is, for example, Divinylbenzene (DVB), Ethyleneglycol dimethacrylate (EGDMA), Triethylene glycol dimethacrylate (TEDMA), or the like, but is not limited thereto.

Thereafter, a polymer layer is formed on the knobby copolymer core. In particular, a charged water-soluble monovinyl monomer, deionized water, and a water-soluble initiator are added and continuously stirred for at least 2 hours at 60 to 90° C. In an embodiment, the aforementioned charged water-soluble monovinyl monomer may be added in an amount of 0.1 to 1 g, and is, for example, acrylic acid, methacrylic acid, 3-aminopropylene/allylamine, sodium allylsulfonate, or the like, but is not limited thereto. Further, the aforementioned deionized water may be added in an amount of 5 to 15 ml. Moreover, the aforementioned water-soluble initiator may be added in an amount of 0.02 to 0.1 g, and is, for example, persulfate, hydrogen peroxide, or the like, but is not limited thereto.

Next, the mixture is cooled to room temperature, and after the reaction was completed, the product was washed with deionized water to obtain the knobby polymer particles having a charged polymer layer on the surface.

Thereafter, a magnetic substance layer is formed on the knobby polymer particles having a charged polymer layer on the surface. Specifically, the knobby polymer particles having a charged polymer layer on the surface, deionized water, ethylene glycol, and a precursor of a magnetic substance are performed to place into a reactor. In an embodiment, the aforementioned knobby polymer particles having a charged polymer layer on the surface may be added in an amount of 0.5 to 2 g. And, the aforementioned deionized water may be added in an amount of 200 to 600 ml. In addition, the aforementioned ethylene glycol may be added in an amount of 0 to 100 ml. In which, the addition of ethylene glycol can be used to regulate the size of the particles coated with the magnetic substance layer. Furthermore, the aforementioned magnetic substance precursor may be added in an amount of 0.05 to 1 g, and is, for example, a precursor of ferrous chloride, cobaltous chloride nickel chloride, or the like, but is not limited thereto.

Subsequently, the aforementioned mixture is stirred and heated to 50-90° C. under a nitrogen atmosphere, and then an aqueous solution of potassium nitrate ($KNO_3$) and hexamethylenetetramine (HMTA) dissolved in deionized water is added. Thereafter, the reaction is performed by continuously stirring at 50 to 90° C. for 0.5 hour or more under a nitrogen atmosphere. After the reaction is completed, the product is washed with deionized water to obtain the knobby polymer particles coated with a magnetic substance layer. In an embodiment, the aforementioned aqueous solution of potassium nitrate and hexamethylenetetramine may be added in an amount of 0.2 to 3 g of potassium nitrate and 2 to 30 g of hexamethylenetetramine dissolved in 20 to 100 ml of deionized water.

Afterward, a silicon-based layer is formed on the knobby polymer particles having the magnetic substance layer formed on the surface. In particular, the knobby polymer particles coated with the magnetic substance layer, deionized water, ethanol, ammonia water or glacial acetic acid, and silane are performed to place into a reactor. In which, ammonia water or glacial acetic acid can be used to hydrolyze silane, so it can be substituted with other substances which can hydrolyze silane. Then, the reaction is performed by stirring at room temperature for 0.5 hour or more. After the reaction is completed, the product was washed with deionized water to obtain the magnetic particles coated with a silicon-based layer.

In an embodiment, the aforementioned knobby polymer particles coated with the magnetic substance layer may be added in an amount of 0.3 to 2 g. And, the aforementioned deionized water may be added in an amount of 0 to 200 ml. In addition, the aforementioned ethanol may be added in an amount of 0 to 600 ml. In which, at least one of deionized water and ethanol may be selected as needed. Further, the aforementioned ammonia water or glacial acetic acid may be added in an amount of 10 to 50 ml. In addition, the aforementioned silane may be added in an amount of 0.1 to 1 ml, and is, for example, TMOS, TEOS, APTES, GOPTS, or the like, but is not limited thereto.

Specific experimental examples are exemplified below to specifically describe a method of manufacturing the magnetic particles.

Example 1

Preparation of knobby styrene/divinylbenzene copolymer core with different ratios and carboxyl polymer layer are illustrated in Examples 1-1, 1-2 and 1-3, respectively.

In Example 1-1, 1.5 ml of deionized water, 39 ml of tert-butanol, 0.34 g of polyvinylpyrrolidone (PVP), 0.92 g of benzoyl peroxide, 10 ml of styrene and 0.1 ml of divinylbenzene are performed to place into a reactor, and the aforementioned mixture is stirred at 70° C. for 22 hours under a nitrogen atmosphere. Thereafter, 0.3 ml of methylacrylic acid (MAA), 10 ml of deionized water and 0.05 g of potassium persulfate ($K_2S_2O_8$) are added, and the reaction is performed by continuously stirring at 70° C. for 2 hours, followed by cooling to room temperature. After the reaction is completed, the product is washed with deionized water to obtain a knobby styrene/divinylbenzene copolymer core having a carboxyl polymer layer. Then, the average diameter D of these knobby copolymer cores and the average height h of the protrusions are observed and measured using a scanning electron microscope (SEM, FEI Quanta 400F).

Figure 2A:
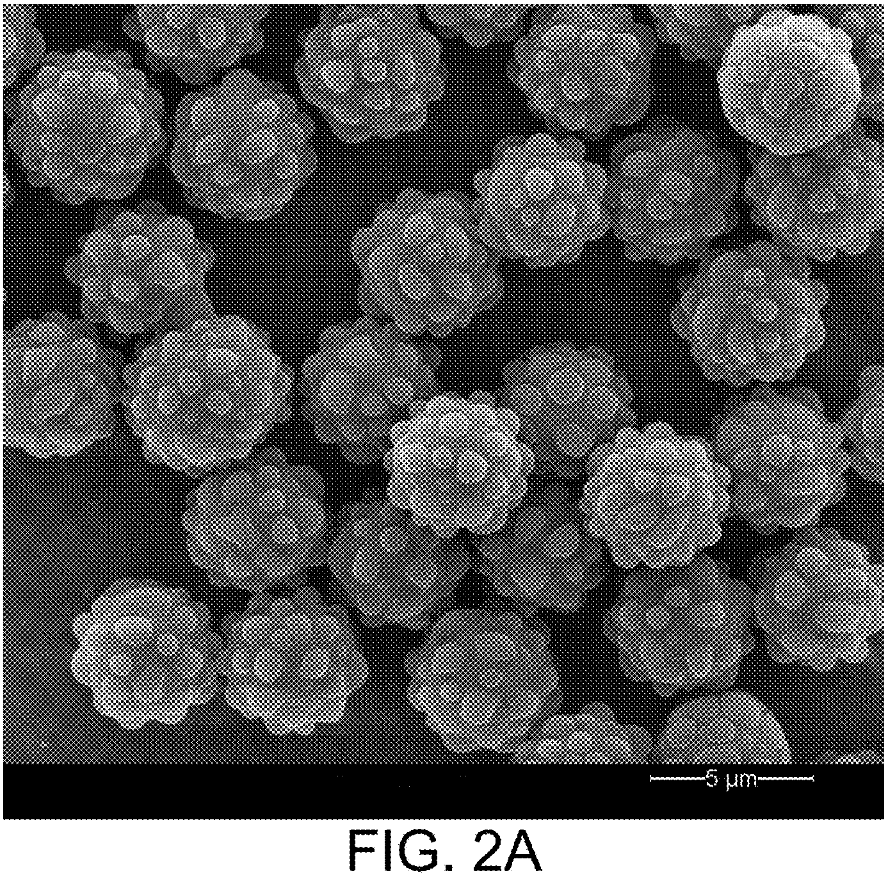
FIG. 2A is a scanning electron micrograph of a knobby copolymer core covered with a polymer layer in accordance with the Example 1-1 of the present disclosure.

The SEM photograph (10000×) of the polymer layer-coated knobby copolymer core obtained according to the aforementioned reaction conditions is as shown in FIG. 2A. In which, the multi-protrusive appearance is illustrated, the average diameter D is measured about 4.5 μm, and average height h of the protrusions is measured about 1000 nm.

In Example 1-2, 2.57 ml of deionized water, 30 ml of ethanol, 0.34 g of polyvinylpyrrolidone, 0.92 g of benzoyl peroxide, 9.5 ml of styrene, and 0.0666 ml of divinylbenzene are performed to place into a reactor, and then the aforementioned mixture is stirred at 70° C. for 22 hours under a nitrogen atmosphere. Thereafter, 0.6 ml of methacrylic acid, 10 ml of deionized water and 0.05 g of potassium persulfate are added, and the reaction is performed by continuously stirring at 70° C. for 2 hours, followed by cooling to room temperature. After the reaction is completed, the product is washed with deionized water to obtain a knobby styrene/divinylbenzene copolymer core having a carboxyl polymer layer. Afterward, the average diameter D of these knobby copolymer cores and the average height h of the protrusions were observed and measured using a scanning electron microscope.

Figure 2B:
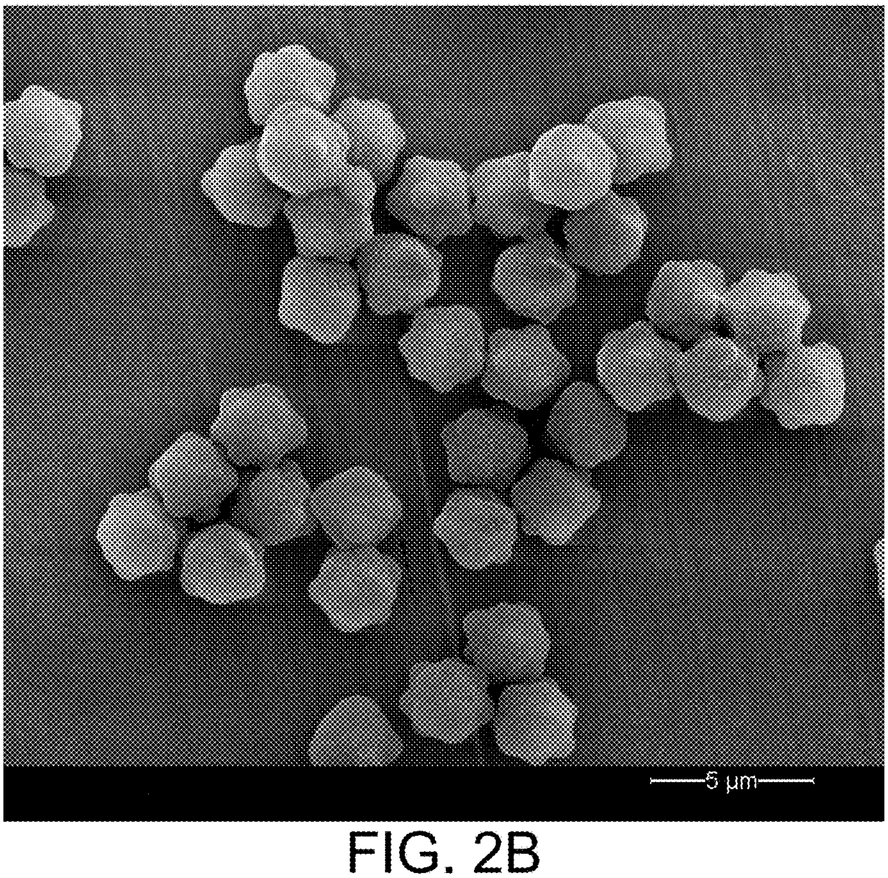
FIG. 2B is a scanning electron micrograph of a knobby copolymer core covered with a polymer layer in accordance with the Example 1-2 of the present disclosure.

The SEM photograph (10000×) of the polymer layer-coated knobby copolymer core obtained according to the aforementioned reaction conditions is as shown in FIG. 2B. In which, the multi-protrusive appearance is illustrated, the average diameter D is measured about 2.5 μm, and average height h of the protrusions is measured about 500 nm. It should be noted that, according to FIG. 2B, when the average diameter D of the magnetic particles is less than 1 μm, the protrusions formed on the surface of the knobby copolymer core are rather limited due to the surface area of the knobby copolymer core is relatively small. That is, it is actually difficult to manufacture the magnetic particles with an average diameter D of less than 1 Therefore, the average diameter D of the magnetic particles of the present invention is, for example, greater than 1 μm.

In Example 1-3, 15 ml of ethanol, 21 ml of ethylene glycol methyl ether, 0.75 g of polyvinylpyrrolidone, 0.5 g of benzoyl peroxide, 7.5 ml of styrene, and 0.105 ml of divinylbenzene are performed to place into a reactor, and the aforementioned mixture is stirred at 70° C. for 22 hours under a nitrogen atmosphere. Thereafter, 0.2 ml of methacrylic acid, 10 ml of deionized water and 0.05 g of potassium persulfate are added, and the reaction is performed by continuously stirring at 70° C. for 2 hours, followed by cooling to room temperature. After the reaction is completed, the product is washed with deionized water to obtain a knobby styrene/divinylbenzene copolymer core having a carboxyl polymer layer. Afterward, the average diameter D of these knobby copolymer cores and the average height h of the protrusions are observed and measured using a scanning electron microscope.

Figure 2C:
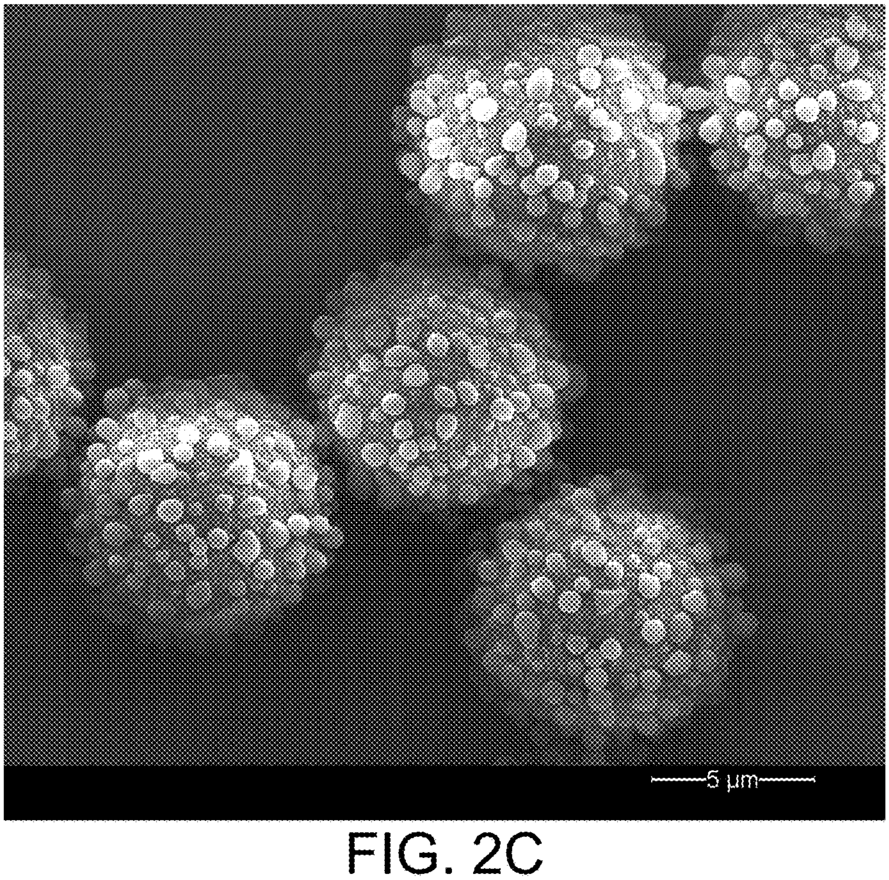
FIG. 2C is a scanning electron micrograph of a knobby copolymer core covered with a polymer layer in accordance with the Example 1-3 of the present disclosure.

The SEM photograph (10000×) of the polymer layer-coated knobby copolymer core obtained according to the aforementioned reaction conditions is as shown in FIG. 2C. In which, the multi-protrusive appearance is illustrated, the average diameter D is measured about 8.5 μm, and average height h of the protrusions is measured about 900 nm.

Example 2

Figure 3:
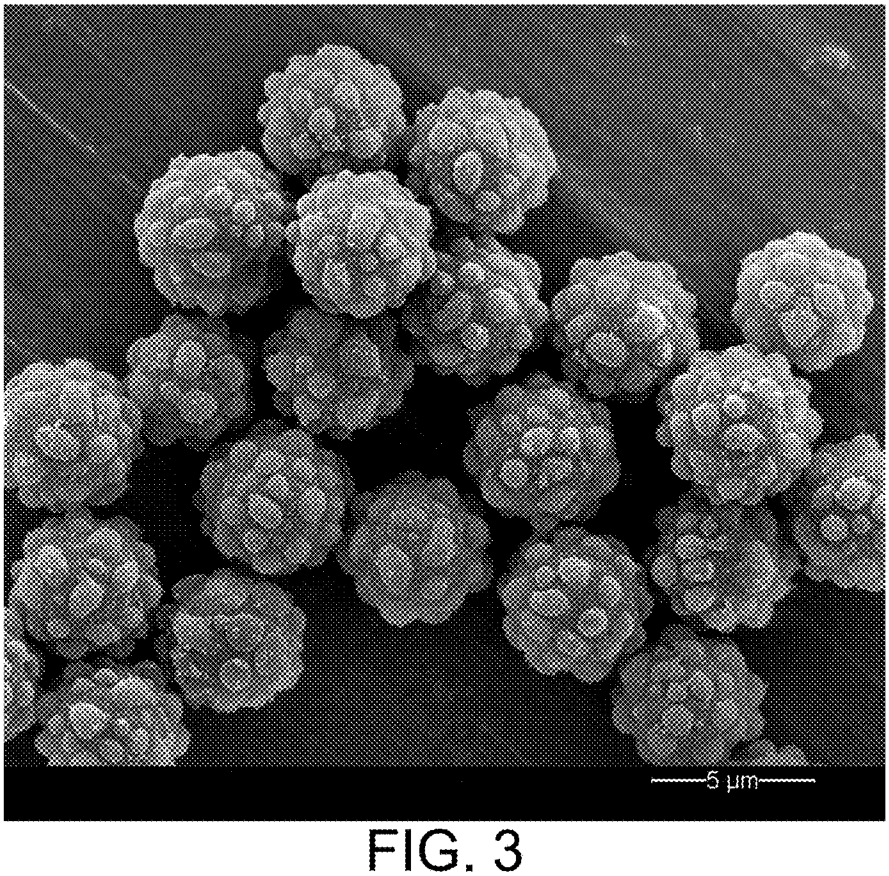
FIG. 3 is a scanning electron micrograph of a knobby copolymer core covered with a polymer layer and a magnetic substance layer in accordance with the Example 2 of the present disclosure.

Preparation of a Magnetic Substance Layer Coated on the Knobby Copolymer Core 1 g of the particles formed in Example 1-1, 400 ml of deionized water, 50 ml of ethylene glycol, and 0.3 g of iron (II) chloride ($FeCl_2$) are performed to place into a reactor, and the aforementioned mixture is stirred and heated to 60° C. under a nitrogen atmosphere. Next, an aqueous solution of 2 g of potassium nitrate and 20 g of hexamethylenetetramine dissolved in 50 ml of deionized water is added, and the reaction is performed by continuously stirring at 60° C. for 1 hour under a nitrogen atmosphere. After the reaction is completed, the product is washed with deionized water to obtain the particles of knobby styrene/divinylbenzene copolymer core having a carboxyl group polymer layer and coated with a magnetic substance layer of iron oxide, and the SEM photograph (10000×) thereof is as shown in FIG. 3. According to FIG. 3, it can be known that the magnetic substance layer does not substantially affect the surface morphology and diameter of the particles.

Example 3

Figure 4:
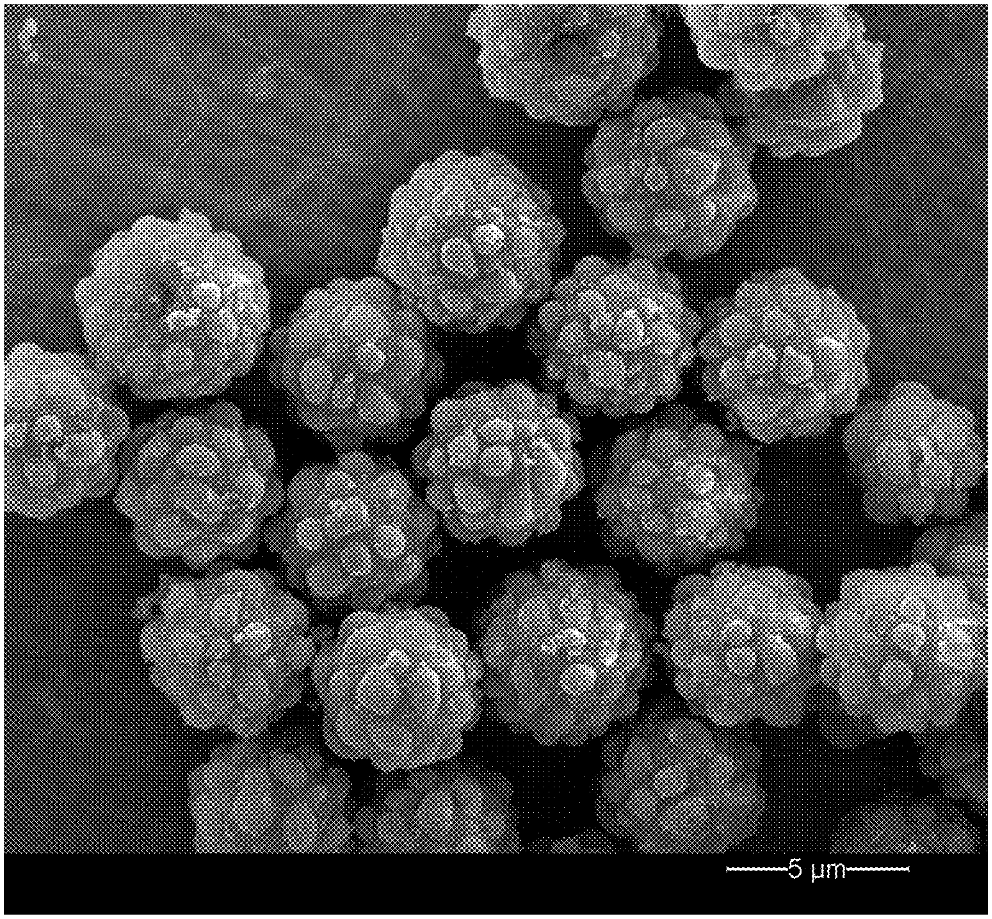
FIG. 4 is a scanning electron micrograph of a magnetic particle in accordance with the Example 3 of the present disclosure.

Preparation of a Silicon-Based Layer Coated on the Magnetic Substance Layer 1 g of the magnetic particles formed in Example 2, 100 ml of deionized water, 500 ml of ethanol, 30 ml of ammonia water, and 0.3 ml of TEOS are performed to place into a reactor, and the reaction is performed by stirring at room temperature for 2 hours. After the reaction is completed, the product was washed with deionized water to obtain the magnetic particles coated with a silicon-based layer, and the SEM photograph (10000×) thereof is as shown in FIG. 4. According to FIG. 4, it can be known that the silicon-based layer does not substantially affect the surface morphology and diameter of the particles.

In summary, the magnetic particle of the present disclosure has a multi-protrusive surface and includes in the order of a knobby copolymer core, a polymer layer, a magnetic substance layer, and a silicon-based layer from the inside to the outside. Since the magnetic particle has multi-protrusive surface, the surface area of the magnetic particle can be greatly increased, thereby contributing to the close packing of the magnetic particles. Furthermore, since the surface of the knobby polymer particles is formed with a polymer layer containing at least one functional group and the functional group may be charged, it is advantageous for the knobby polymer particles to adsorb more magnetic substance precursors. Accordingly, the effect of high magnetic quantization is achieved. In this way, the magnetic particles can be widely applied to the field of biomedicine, such as immune-quantitative analysis, purification and separation, or cell stimulation and amplification.

It will be apparent to those skilled in the art that various modifications and variations may be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A manufacturing method of a magnetic particle with multi-protrusive surface, comprising:

polymerizing at least two lipid-soluble monomers into a copolymer using a lipid-soluble initiator to form a copolymer core having a plurality of protrusions on a surface of the copolymer core, wherein the at least two lipid-soluble monomers comprise a monofunctional monomer and a bifunctional monomer, wherein the monofunctional monomer is styrene and the bifunctional monomer is divinylbenzene, and wherein the average height of the plurality of protrusions ranges from 100 nm to 5000 nm;

forming a polymer layer to cover the plurality of protrusions on the surface of the copolymer core, wherein the polymer layer having at least one functional group, wherein the at least one functional group is negatively charged and wherein a material of the polymer layer is different from a material of the copolymer core;

adsorbing a magnetic substance precursor onto the polymer layer via the negatively charged at least one functional group to form a magnetic substance layer with a plurality of protrusions thereon entirely covering the polymer layer, wherein the thickness of the magnetic substance layer ranges from 20 nm to 200 nm; and forming a silicon-based layer to cover the magnetic substance layer, wherein the thickness of the silicon-based layer ranges from 1 nm to 50 nm.

2. The manufacturing method of the magnetic particle with multi-protrusive surface of claim 1, wherein a volume percentage of the bifunctional monomer relative to the monofunctional monomer is 0.4% to 2%.

3. The manufacturing method of the magnetic particle with multi-protrusive surface of claim 1, wherein a volume percentage of the bifunctional monomer relative to the monofunctional monomer is 0.5% to 1.8%.

4. The manufacturing method of the magnetic particle with multi-protrusive surface of claim 1, wherein a volume percentage of the bifunctional monomer relative to the monofunctional monomer is 0.6% to 1.5%.

5. The manufacturing method of the magnetic particle with multi-protrusive surface of claim 1, wherein the at least one functional group comprises a carboxyl group.

6. The manufacturing method of the magnetic particle with multi-protrusive surface of claim 1, wherein the magnetic substance layer comprises an iron ion ($Fe^{2+}$), a cobalt ion ($Co^{2+}$0), a nickel ion ($Ni^{2+}$), or a combination thereof.

7. The manufacturing method of the magnetic particle with multi-protrusive surface of claim 1, wherein the magnetic substance precursor comprises ferrous chloride, cobalt chloride, or nickel chloride.

8. The manufacturing method of the magnetic particle with multi-protrusive surface of claim 1, wherein the silicon-based layer comprises siloxane, silica glass, silicon oxide, silicate salt or a combination thereof.

* * * * *